(12) United States Patent
Wang

(10) Patent No.: US 11,109,889 B2
(45) Date of Patent: Sep. 7, 2021

(54) DOUBLE-SIDED NEEDLE GROOVE, FRAME BODY AND PUNCTURE FRAME

(71) Applicant: Qin Wang, Jiangsu (CN)

(72) Inventor: Qin Wang, Jiangsu (CN)

( * ) Notice: Subject to any disclaimer, the term of this patent is extended or adjusted under 35 U.S.C. 154(b) by 242 days.

(21) Appl. No.: 16/091,461

(22) PCT Filed: Apr. 5, 2016

(86) PCT No.: PCT/CN2016/078450
§ 371 (c)(1),
(2) Date: Oct. 4, 2018

(87) PCT Pub. No.: WO2017/173569
PCT Pub. Date: Oct. 12, 2017

(65) Prior Publication Data
US 2019/0150976 A1    May 23, 2019

(51) Int. Cl.
*A61B 17/34* (2006.01)
*A61B 90/11* (2016.01)

(52) U.S. Cl.
CPC .......... *A61B 17/3403* (2013.01); *A61B 17/34* (2013.01); *A61B 90/11* (2016.02);
(Continued)

(58) Field of Classification Search
CPC ................ A61B 17/3403; A61B 17/34; A61B 2017/3413; A61B 2017/3411; A61B 90/11
See application file for complete search history.

(56) References Cited

U.S. PATENT DOCUMENTS 4,489,730 A * 12/1984 Jingu .................. A61B 8/0833
600/461
5,052,396 A * 10/1991 Wedel ................ A61B 1/00142
600/461

FOREIGN PATENT DOCUMENTS

CN    202060888 U    12/2011
CN    105902301 A    8/2016

OTHER PUBLICATIONS

English Translation of CN105902301A (Google Translate).
(Continued)

*Primary Examiner* — Anh T Dang
(74) *Attorney, Agent, or Firm* — David W. Carstens; James D. Tuck; Carstens & Cahoon, LLP

(57) ABSTRACT

A double-sided needle groove, a frame body and a puncture frame, wherein the double-sided needle groove has an axisymmetric outer contour, and is provided at one side with at least one needle slot a (1) and at the other side with at least one needle slot b (2); and the needle slot b (2) is fan-shaped. The double-sided needle groove is provided with one or more needle slots a (1) having a fixed needle insertion angle and a needle slot b (2) having an adjustable needle insertion angle, and the needle slot a (1) and the needle slot b (2) respectively correspond to the diameters of puncture needles and may be designed to meet multiple width specifications. During the performance of a B-ultrasound puncture operation, based on operation requirements of a surgeon for a fixed or adjustable angle, there is only a need to switch front and back sides of the double-sided needle groove, thus avoiding the need for an additional puncture frame, and switch the needle slots according to the diameters of the puncture needles. As can be seen, the double-sided needle groove can be applied to various types of B-ultrasound puncture operations and can effectively reduce the number of accessories in the puncture operations, thereby providing fast installation, saving resources and reducing costs.

6 Claims, 3 Drawing Sheets

(52) U.S. Cl.
CPC ............... *A61B 2017/3411* (2013.01); *A61B 2017/3413* (2013.01)

(56) References Cited

OTHER PUBLICATIONS

English Translation of CN202060888U (Google Translate).
International Search Report for International Application No. PCT/CN2016/078450, ISA/CN dated Dec. 27, 2016 (With English Translation).

* cited by examiner

DOUBLE-SIDED NEEDLE GROOVE, FRAME BODY AND PUNCTURE FRAME

FIELD OF THE INVENTION

The present invention relates to the technical field of in vitro puncture frames required for ultrasonic B-ultrasound puncture operations, and specifically relates to a double-sided needle groove, a frame body and a puncture frame.

TECHNICAL BACKGROUND

The current in vitro puncture frames generally control the needle insertion in two ways: 1. using a rotating needle slot structure; and 2. using a single needle groove structure. The single needle groove generally has two forms: 1. a needle groove directly having a fixed needle insertion angle; and 2, a needle groove with adjustable needle insertion angle. Both of the needle grooves have apertures of different specifications for one-to-one correspondence to puncture needles of different diameters, so each puncture frames using the single needle groove structure must be equipped with needle grooves of various aperture specifications. In a B-ultrasound puncture operation, the surgeon would select, according to the clinical use, a needle groove with different apertures having a fixed needle insertion angle or a needle groove with different apertures having an adjustable needle insertion angle for the B-ultrasound operation. Therefore, the increase in the accessories would increase costs in the B-ultrasound puncture operation of a patient and waste resources.

SUMMARY OF THE INVENTION

In order to overcome those technical defects, i.e., having a multitude of accessories, increasing operation costs and easily resulting in waste of resources, in puncture operations of the prior art, the present invention provides a double-sided needle groove, a frame body and a puncture frame, which are designed as front-back interlocking structures, and thus can reduce the number of the double-sided needle groove required for the puncture operations so as to accomplish the purposes of providing fast installation, saving resources and reducing costs in the B-ultrasound puncture operations.

In order to achieve the above purposes, the technical solution adopted by the present invention is:
a double-sided needle groove, which has an axisymmetric outer contour, and is provided at one side with at least one needle slot a and at the other side with at least one needle slot b.

Preferably, the needle slot b is fan-shaped.

The double-sided needle groove is provided with one or more needle slots a (the needle slot with a fixed needle insertion angle) and needle slots b (the needle slot with an adjustable needle insertion angle), and the needle slot a and the needle slot b respectively correspond to the diameters of puncture needles and may be designed to meet multiple width specifications. When there is a need to perform different B-ultrasound puncture operations, there is only a need to switch front and back sides of the double-sided needle groove and switch the needle slots according to the diameters of the puncture needles. As can be seen, the double-sided needle groove can be applied to various types of B-ultrasound puncture operations and can effectively reduce the number of accessories in the puncture operations, thereby providing fast installation, saving resources and reducing costs.

Preferably, the number of the needle slot a is three, and the number of the needle slot b is one.

Further, the double-sided needle groove is respectively provided, at two sides thereof, a rotating convex half shaft a and a rotating convex half shaft b, which are symmetric about a centerline of the outer contour of the double-sided needle groove.

Further, the rotating convex half shaft a and the rotating convex half shaft b are respectively provided with a notch a and a notch b, which are symmetric about the centerline of the outer contour of the double-sided needle groove.

A frame body for installing a double-sided needle groove according to any one of the above, wherein the frame body is provided with a needle insertion plate in cooperation with the double-sided needle groove.

Further, the needle insertion plate is provided at one side with a rotating concave half shaft in cooperation with the rotating convex half shaft a or rotating convex half shaft b and at the other side with a hook in cooperation with the rotating convex half shaft a or rotating convex half shaft b.

Further, the hook is provided with a boss in cooperation with the notch a or notch b. The boss is provided with a pit. The pit allows the user to manually remove the double-sided needle groove from the frame body.

Further, the needle insertion plate is provided at the bottom with an elastic piece, and a bump is disposed at a position on the elastic piece in correspondence to the rotating convex half shaft a or rotating convex half shaft b.

A puncture frame comprising a double-sided needle groove according to any one of the above and a frame body according to any one of the above.

The puncture frame can realize the separation of the double-sided needle groove and the entire frame body. When the surgeon needs to insert the needle into the human body at a fixed angle in the operation, a needle slot surface with a fixed angle (a surface with the needle slot a) may be used for cooperation. When the surgeon needs to insert the needle into the human body at an adjustable angle in the operation, a needle slot surface with an adjustable angle (a surface with the needle slot b) may be used for cooperation. Meanwhile, it is possible to control the requirements of fixed-angle needle insertion and free-angle needle insertion sides for different needle diameters by replacement with new needle slots of different specifications.

The present invention has the following advantageous effects: the double-sided needle groove of the present invention is provided with one or more needle slots a (the needle slot with a fixed needle insertion angle) and needle slots b (the needle slot with an adjustable needle insertion angle), and the needle slot a and the needle slot b respectively correspond to the diameters of puncture needles and may be designed to meet multiple width specifications. When there is a need to perform different B-ultrasound puncture operations, there is only a need to switch front and back sides of the double-sided needle groove and switch the needle slots according to the diameters of the puncture needles. As can be seen, the double-sided needle groove can be applied to various types of B-ultrasound puncture operations and can effectively reduce the number of accessories in the puncture operations, thereby providing fast installation, saving resources and reducing costs.

In the figures, 1—needle slot a; 2—needle slot b; 3—rotating convex half shaft a; 31—notch a; 4—rotating convex half shaft b; 41—notch h; 5—needle insertion plate; 51—rotating concave half shaft; 52—hook; 521—boss; 5211—pit; 53—elastic piece; 531—bump; 54—needle insertion plane.

DETAILED DESCRIPTION OF THE EMBODIMENTS

Hereinafter, the structures of the present invention will be explained in detail with reference to the figures.

Figure 1:
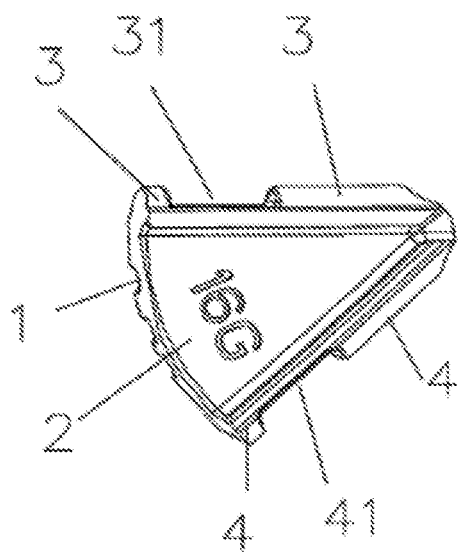
FIG. 1 is a front view of a double-sided needle groove according to an embodiment of the present invention.
Figure 2:
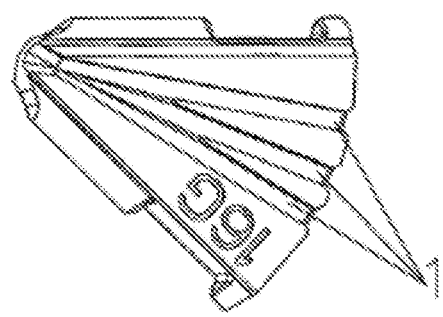
FIG. 2 is a rear view of the double-sided needle groove according to the embodiment of the present invention.
Figure 3:
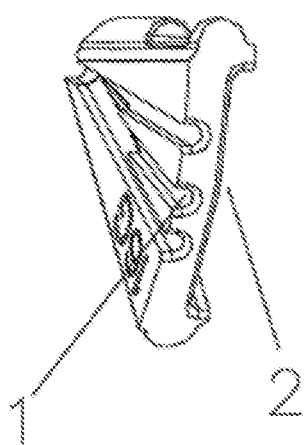
FIG. 3 is a structural schematic diagram of the double-sided needle groove according to the embodiment of the present invention.

As shown in FIGS. 1-3, the present invention provides a double-sided needle groove, wherein the double-sided needle groove, which has a "fan-like" outer contour, is provided at one side with three needle slots a1, and the three needle slots a1 may be designed to meet multiple specifications so that apertures thereof are in one-to-one correspondence to the diameters of puncture needles; and the double-sided needle groove is provided at the other side with one fan-shaped (a certain angle range may be provided) needle slot b2, and the needle slot b2 may be designed to meet multiple width specifications so that dimensions thereof are in one-to-one correspondence to the diameters of the puncture needles.

The double-sided needle groove of the present invention is provides a rotating convex half shaft a3 and a rotating convex half shaft b4, on each side respectively, which are symmetric about a centerline of the outer contour of the double-sided needle groove. The rotating convex half shaft a3 and the rotating convex half shaft b4 are respectively provided with a notch a31 and a notch b41, which are symmetric about the centerline of the outer contour of the double-sided needle groove.

It is understood by those skilled in the art, that the number of the needle slot a1 of the double-sided needle groove provided by the present invention may be one, two, three, four or more. The specific number can be set according to the actual production and application requirements.

Figure 4:
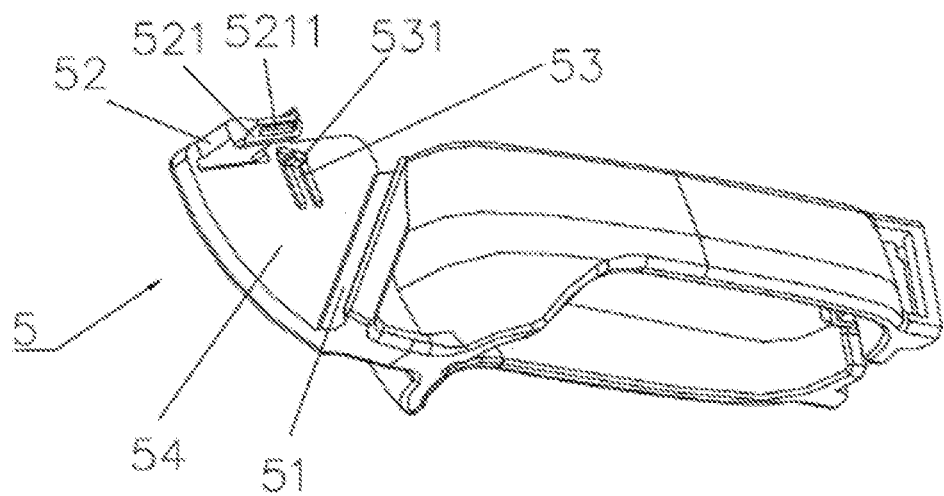
FIG. 4 is a structural schematic diagram of a frame body according to an embodiment of the present invention.

As shown in FIG. 4, the present invention provides a frame body for installing the above double-sided needle groove, wherein the frame body is provided with a needle insertion plate 5 in cooperation with the double-sided needle groove. The needle insertion plate 5 is provided at one side with a rotating concave half shaft 51 in cooperation with the rotating convex half shaft a3 or rotating convex half shaft b4, and at the other side with a hook 52 in cooperation with the rotating convex half shaft a3 or rotating convex half shaft b4. The hook 52 is provided with a boss 521 in cooperation with the notch a31 or notch b41. The boss 521 is provided with a pit 5211.

The needle insertion plate 5 is provided at the bottom with an elastic piece 53, and a bump 531 is disposed at a position on the elastic piece 53 in correspondence to the rotating convex half shaft a3 or rotating convex half shaft b4.

The rotating concave half shaft 51 and the hook 52 are used for fixing the double-sided needle groove. The pit 5211 on the boss 521 allows the user to manually remove the double-sided needle groove from the frame body. The bump 531 on the elastic piece 53 is used to eject the double-sided needle groove when it is removed.

Figure 5:
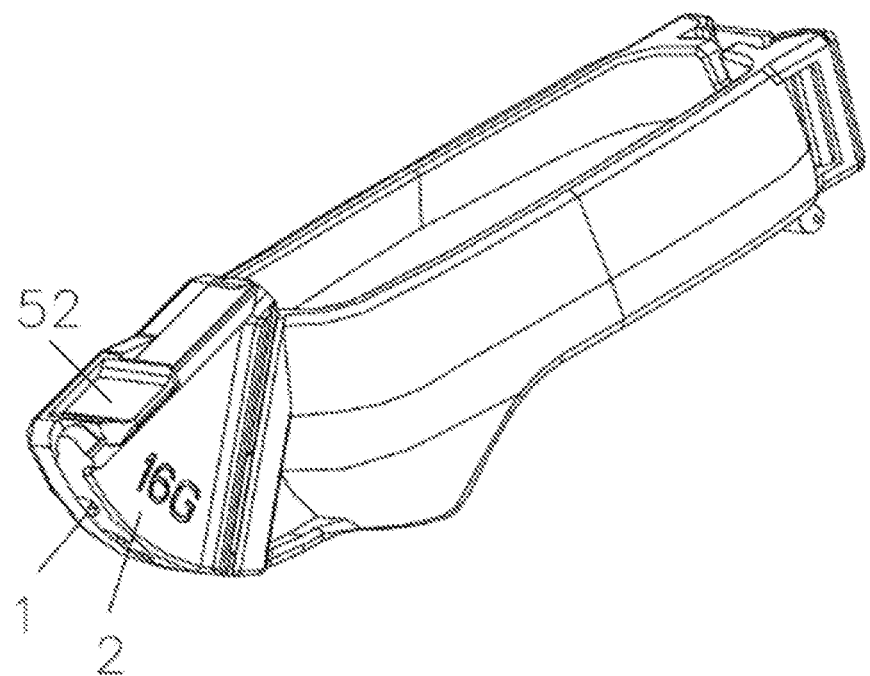
FIG. 5 is a structural schematic diagram (a fixed needle insertion angle side) of a puncture frame according to an embodiment of the present invention.
Figure 6:
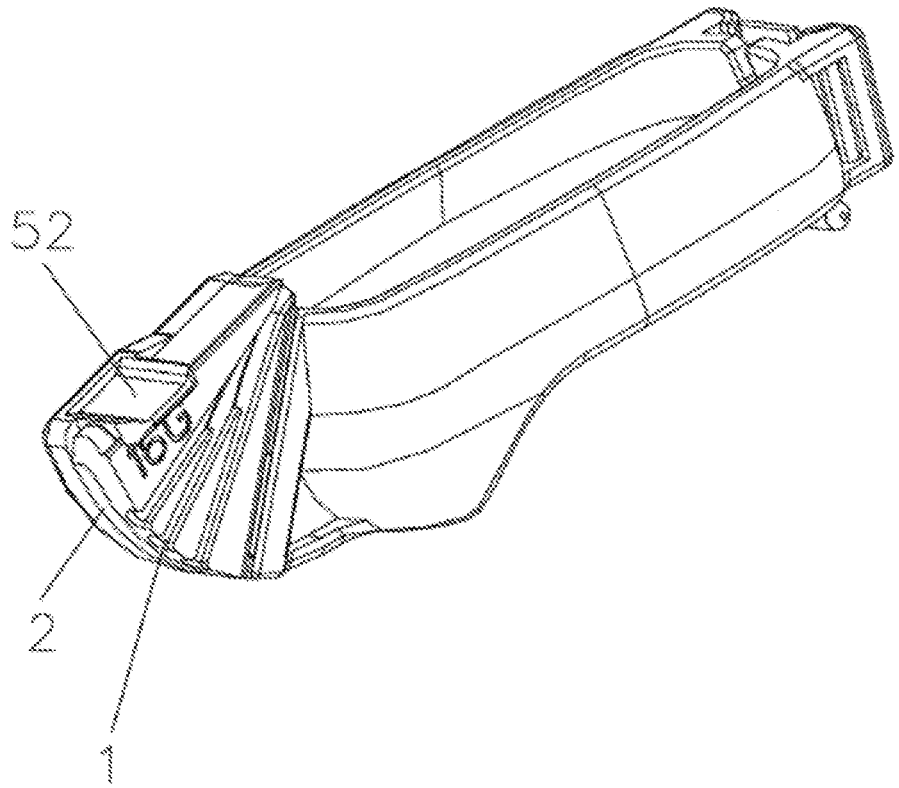
FIG. 6 is a structural schematic diagram (an adjustable needle insertion angle side) of the puncture frame according to the embodiment of the present invention.

As shown in FIGS. 5-6, the present invention provides a puncture frame comprising a double-sided needle groove according to any one of the above and a frame body according to any one of the above. The specific use methods are as follows:

I. A use method of the fixed needle insertion angle side of the double-sided needle groove: first installing the frame body on an ultrasonic probe, selecting a double-sided needle groove of a required aperture, aligning the rotating convex half shaft b4 on the double-sided needle groove into the rotating concave half shaft 51 on the frame body, then aligning the notch a31 on the double-sided needle groove with the boss 521 on the frame body, and pressing the double-sided needle groove hard to deform the hook 52 outwardly to fit. Then buckle in and install the double-sided needle groove and the needle insertion plane 54 of the needle insertion plate 5 in place, so that the resultant structure, after the installation, is as shown in FIG. 5. At this time, the needle slot a1 with a fixed needle insertion angle is fitted to the needle insertion plane 54 so as to accomplish the purpose of needle insertion at a fixed angle.

II. A use method of the adjustable needle insertion angle side of the double-Sided needle groove: first installing the frame body on an ultrasonic probe, selecting a double-sided needle groove of a required aperture, aligning the rotating convex half shaft a3 on the double-sided needle groove into the rotating concave half shaft on the frame body, then aligning the notch b41 on the double-sided needle groove with the boss 521 on the frame body, and pressing the double-sided needle groove hard to deform the hook 52 outwardly to fit. Then buckled in and install the double-sided needle groove and the needle insertion plane 54 of the needle insertion plate 5 in place, so that the resultant structure, after the installation, is as shown in FIG. 6. At this time, the needle slot b2 with an adjustable needle insertion angle is fitted to the needle insertion plane 54 so as to accomplish the purpose of needle insertion at an adjustable angle.

After the puncture operation is completed, the pit 5211 on the hook 52 is held by hand(s), so as to apply a force outwardly, thus deformed the hook 52. This in turn causes the bump 531 on the needle insertion plate 5 to eject and takes off the double-sided needle groove.

The above are only preferred embodiments of the present invention and are not intended to limit the present invention. Any modifications, equivalent substitutions, simple improvements and the like made in the essential contents of the present invention shall be included in the scope of protection of the present invention.

The invention claimed is:

1. A frame body for installing a double-sided needle groove comprising a needle insertion plate (5) in cooperation with the double-sided needle groove having an axisymmetric outer contour, and provided at one side with at least one needle slot a (1) and at the other side with at least one needle slot b (2), wherein the double-sided needle groove is respectively provided, at two sides thereof, a rotating convex half shaft a (3) and a rotating convex half shaft b (4), which are symmetric about a centerline of the outer contour of the double-sided needle groove, and the needle insertion plate (5) is provided at one side with a rotating concave half shaft (51) in cooperatiOn with the rotating convex half shaft a (3)

or rotating convex half shaft b (4), and at the other side with a hook (52) in cooperation with the rotating convex half shaft a (3) or rotating convex half shaft b (4), the rotating convex half shaft a (3) and the rotating convex half shaft b (4) are provided with a notch a (31) and a notice h (41) respectively, which are symmetric about the centerline of the outer contour of the double-sided needle groove, and the hook (52) is provided with a boss (521) in cooperation with the notch a (31) or notch b (41).

2. The frame body according to claim 1, characterized in that, the boss (521) is provided with a pit (5211).

3. The frame body according to claim 2, characterized in that, the needle insertion plate (5) is provided at the bottom with an elastic piece (53), and a bump (531) is disposed at a position on the elastic piece (53) in correspondence to the rotating convex haft shaft a (3) or rotating convex half shaft b (4).

4. A puncture frame comprising a double-sided needle groove having an axisymmetric outer contour and provided at one side with at least one needle slot a (1) and at the other side with at least one needle slot b (2), and a frame body having a needle insertion plate (5) in. cooperation with the double-sided needle groove, wherein the needle slot b (2) is fan-shaped, the number of the needle slot a (1) is three, and the number of the needle slot b (2) is one, the double-sided needle groove is respectively provided, at two sides thereof, a rotating convex half shaft a (3) and a rotating convex half shaft b (4), which are symmetric about a centerline of the outer contour of the double-sided needle groove, the needle insertion plate (5) is provideed at one side with a rotating concave half shaft (51) in cooperation with the rotating convex half shaft a (3) or rotating convex half shaft b (4) and at the other side with a hook (52) in cooperation with the rotating convex half shaft a (3) or rotating convex half shaft b (4), the rotating convex half shaft a (3) and the rotating convex half shaft b (4) are provided with a notch a (31) and a notch b (41) respectively, which are symmetric about the centerline of the outer contour of the double-sided needle groover, and the hook (52) is provided with a boss (521) in cooperation with the notch a (31) or notch b (41).

5. The frame body according to claim 4, characterized in that, the boss (521) is provided with a pit (5211).

6. The frame body according to claim 4, characterized in that, the needle insertion plate (5) is provided at the bottom with an elastic piece (53), arid a bump (531) is disposed at a position on the elastic piece (53) in correspondence to the rotating convex half shaft a (3) or rotating convex half shaft b (4).

\* \* \* \* \*